United States Patent [19]

Rieselman

[11] 4,183,140
[45] Jan. 15, 1980

[54] DENTAL STAIN REMOVER

[75] Inventor: Robert H. Rieselman, Clearwater, Fla.

[73] Assignee: Concept Inc., Clearwater, Fla.

[21] Appl. No.: 882,634

[22] Filed: Mar. 2, 1978

Related U.S. Application Data

[63] Continuation-in-part of Ser. No. 788,700, May 31, 1977, Pat. No. Des. 250,662.

[51] Int. Cl.² .............................................. A61C 3/06
[52] U.S. Cl. .................................... 32/59; 32/DIG. 3
[58] Field of Search ................. 32/59, 58, 27, DIG. 3, 32/DIG. 8; 128/62 A, 56

[56] References Cited

U.S. PATENT DOCUMENTS

| | | | |
|---|---|---|---|
| 1,621,190 | 3/1927 | Brown | 32/27 |
| 2,861,462 | 11/1958 | Hussar | 32/DIG. 8 |
| 3,092,908 | 6/1963 | Flatland | 32/27 |
| 3,163,934 | 1/1965 | Wiseman | 32/27 |
| 3,210,848 | 10/1965 | Bizzigotti | 32/27 |
| 3,244,846 | 4/1966 | Kopp | 32/27 |
| 4,004,344 | 1/1977 | Gold et al. | 32/59 |

*Primary Examiner*—Louis G. Mancene
*Assistant Examiner*—John J. Wilson
*Attorney, Agent, or Firm*—Gipple & Hale

[57] ABSTRACT

A dental stain remover apparatus for removing stains from teeth comprising a drive casing with a removable handle mounted to the drive casing at an angle to the axis of the drive casing, the drive casing forming a chamber which receives a motor and defining a body, nose section, base and cap switch assembly. Batteries are mounted in the handle casing and are electrically connected to the motor by means of the handle casing and a lever switch which extends from the cap switch assembly in the same direction as the handle casing. The motor drives a shaft which is in turn connected to a spindle holding a polishing cup configured to hold the polishing dentifrice. The drive casing and handle are one piece assemblies and are sealed to prevent entrance of foreign material by screwing the handle casing to the drive casing.

9 Claims, 9 Drawing Figures

DENTAL STAIN REMOVER

RELATED APPLICATIONS

This application is a continuation-in-part application of the U.S. Design patent application Ser. No. 788,700 filed May 31, 1977, and now U.S. Pat. No. D250662, issued Apr. 18, 1977.

BACKGROUND OF THE INVENTION

The use of dental stain remover instruments to clean and polish teeth has until recently been performed by dentists using complex, cumbersome and expensive machinery.

It has been common practice to drive such dental stain removing instruments by transmitting power from an electric motor through an endless belt to the hand piece. Alternatively, compressed air from an air compressor is fed to a rotary vane wheel disposed within an instrument hand piece through a length of flexible hose to transmit the required power to the hand piece of the dental instrument. Consequently, these dental instruments are separated from their source of power resulting in a large and bulky apparatus which is cumbersome to work with and cannot be used by the average consumer. Further, the use of an endless belt or length of flexible hose as a power transmission mechanism causes not only a frictional power loss, but takes up a large amount of room. Therefore any person who is required to use such an instrument often finds himself or herself having to assume awkward and unbalanced positions. In addition, any mechanical vibration of the belt or hose involved is transmitted to the hand and on to the mouth. Thus it can be seen that a need has developed for a smaller, simpler portable dental apparatus which does not require technical skill to operate.

The invention generally pertains to portable dental devices and in particular relates to a portable self contained hand held battery powered dental apparatus for removing stains from teeth. The invention specifically provides for a dental device for removing stains from the teeth of a user of the device, which device can be manipulated and activated by grasping the apparatus with one hand. The mechanism is geometrically contoured in an optimal manner for easy manipulation by an individual allowing easy access to the users teeth. The invention is further directed towards dental stain removing devices which can be carried by the individual and used at home or work by the individual for periodic removal of stains from his or her teeth.

PRIOR ART

Dental devices for removing stains from teeth are well known in the art. Some of the prior art dental devices utilize motors which are mounted in the handle portion of the device. A typical device of this nature is disclosed by U.S. Pat. No. 3,509,629 a dental polishing instrument which has a contour angle head member attached to the handle housing. The handle housing contains a battery and a motor which drives a drill bit removably mounted at the exposed end of the head member through a complex linkage. Such linkages increase manufacturing costs of prior art devices and in some cases have been found to reduce reliability of the prior art devices and on occasion to provide safety problems.

It is also noted in such devices where the motor is maintained in the handle section of the device that manipulation in one hand of the user is extremely difficult because of weight distribution and balance problems of the device.

In other prior art devices, the head member projects substantially perpendicular to the handle portion of the dental device. This geometric contouring provides for an unnatural and hard to control motion in the cleaning of the teeth of an operator and may affect the dental stain removing process. A dental stain remover having this type of configuration is shown by U.S. Pat. No. 2,911,660. This reference discloses an angular configured battery powered toothbrush having a motor at the top of the body housing and is alternatively provided with a rigid or flexible neck extending outwardly at right angles from the body housing. The neck holds the stem of a brush used in the apparatus with the brush being driven by a coiled spring drive attached to the motor shaft and the end of the brush. A manually operated rotatable knob switch is located at the base of the handle to activate and deactivate the apparatus and batteries are loaded into and removed from the handle by way of a bayonet locking cap. In such devices a certain amount of skill is needed to optimize the stain removing capability of the device which decreases the number of people who can effectively use these devices. It should further be noted that where an on/off switch is provided which cannot be instantaneously cut off by the user, health hazards can develop. In such instances when an individual is polishing his or her teeth the instrument may slide off the teeth into the mouth and if the instrument cannot be immediately deactivated chipping of the teeth and/or abrasions of the inner mouth surface can result. As an additional feature it should be noted that where simple on/off switches are provided that this causes unnecessary wear on the batteries causing the apparatus to run down more quickly than if the apparatus was provided with an instantaneous turn off switch.

In other prior art reference such as U.S. Pat. No. 4,004,344 a dental stain remover apparatus is disclosed which is geometrically configured to allow an individual user to reach his or her teeth. This apparatus suffers from a contamination problem in that water, dental materials and other waste can enter through the shaft cavity to foul the motor, electrical leads and batteries or breed bacteria in the housing cavity. It should also be noted that in this reference that internal wires are connected from the motor to the batteries. Movement of the motor and switch can cause electrical disconnection as the dental stain remover instrument is handled and used requiring increased maintenance or malfunctioning of the instrument.

Activation of the instrument is accomplished by pressing a switch with either the forefinger or index finger of the hand. A user's finger quickly becomes tired in such an operation because of the continued pressure required to be placed on the switch. In addition the saliva, dentifrice spray and water make finger to switch contact pressure more difficult as well as the problem of such usage causing material to enter into the housing through the switch stem channel. In addition the apparatus cannot be rinsed after use because water will enter the housing.

In all of the above disclosed prior art, switches are placed on the handle to activate the motor, which switches can be fouled by battery corrosion, waste produced during polishing of the teeth or moisture entering the body housing. Furthermore, it has been found in extensive clinical testing that persons polishing their teeth tend to grasp the instrument firmly in one hand leaving one finger free to rest on the barrel of the head to guide the polishing cup or brush along the teeth surface. Thus the switch as shown in the prior art devices cannot be effectively utilized in the normal activation of the average user in polishing his or her teeth.

SUMMARY OF THE INVENTION

A dental stain remover apparatus for removing stains from teeth comprising a head member with a handle formed at an angle to the head member, the head member forming a chamber which receives a motor. Batteries are mouned in the handle casing and are electrically connected to the motor by means of the housing casing and a lever switch which extends from the head member along the handle casing. The motor drives a shaft which is in turn connected to a cupholder which is connected to a polishing cup configured to hold the polishing dentirice with the head member and handle being sealed to prevent entrance of foreign material by screwing the handle casing on the head member.

BRIEF DESCRIPTION OF THE DRAWINGS

The aforementioned features, improvements and objects of the present invention will become more apparent by reference to the following descriptions taken in conjunction with the accompanying drawings, wherein like referenced numerals denote like elements in which.

DESCRIPTION OF THE PREFERRED EMBODIMENTS

Figure 1:
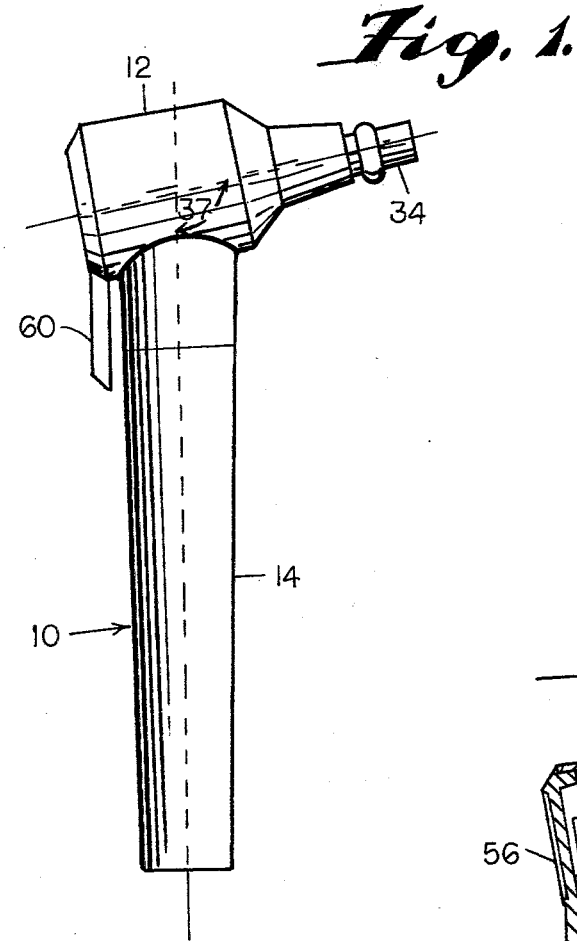
FIG. 1 is a perspective view of the dental stain remover apparatus.

As shown in the drawings and referring specifically to FIGS. 1, 2, 3, and 4, there is disclosed a dental instrument 10 for use by an operator in removing stains from teeth. The instrument disclosed is small in size, substantially the size of FIG. 1, is light in weight and convenient for carrying in an attache case, shaving or cosmetic kit or for use in the home. In operation the dental instrument 10 is designed to remove stains from the outer surfaces of a user's teeth which have developed over a period of time from smoking, drinking coffee, tea or other dentrifice coating activities. The instrument is specifically designed for consumer use, so that any operator can use the instrument without professional training with the use of only one hand.

The dental instrument comprises a housing 11 divided into a head section 12 and a handle section 14. The head section 12 comprises a motor or drive casing 16 which defines a nose 15, a tubular base 36 and a chamber 17 into which motor 18 may be placed. In general a number of well known motors 18 may be used in the invention. However one motor successfully used is a Mabuchi RE-140-18100 with a grounded positive terminal 19 and a protruding negative terminal 21. The negative terminal is bent toward the center of the end bell of the motor. A plurality of four equidistant spaced ribs 20 are formed on the inside of the drive casing 16 to hold the motor in a fixed position inside chamber 17. The inner edges of opposing ribs 20 are parallel with the height of the rib decreasing as it nears the nose of the drive casing. Drive end 22 of the motor 18 is positioned adjacent an annular stop 23 protruding into the motor chamber and formed by the drive casing. The motor is cushioned against a rubatex G-207-N neoprene washer 24 which rests on annular stop 23. The motor chamber 17 is sealed from outside contamination by a teflon motor shaft seal 26 defining an aperture which snugly fits around the shaft 30. The neoprene washer 24 and teflon seal 26 form an effective seal to prevent foreign materials from entering the nose of the casing into the motor chamber to foul or ruin the motor. The motor shaft 30 has mounted thereon a cup holder spindle 32 constructed of ABS plastic which is force fit over the motor shaft 30. The cup holder spindle is provided with an integral annular radially extending flange 33 which extends beyond the casing nose aperture 35 to further act to prevent foreign materials from entering the motor chamber. The cup holder spindle 32 is adapted to receive and hold a flexible rubber removable cup member which is configured to hold a dentifrice material in its cup shaped interior.

Figure 2:
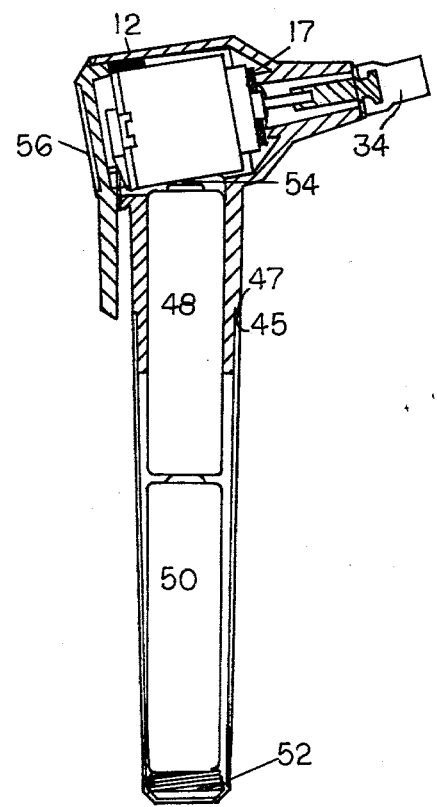
FIG. 2 is a cross-section of the dental apparatus shown in FIG. 1 showing the internal elements.
Figure 3:
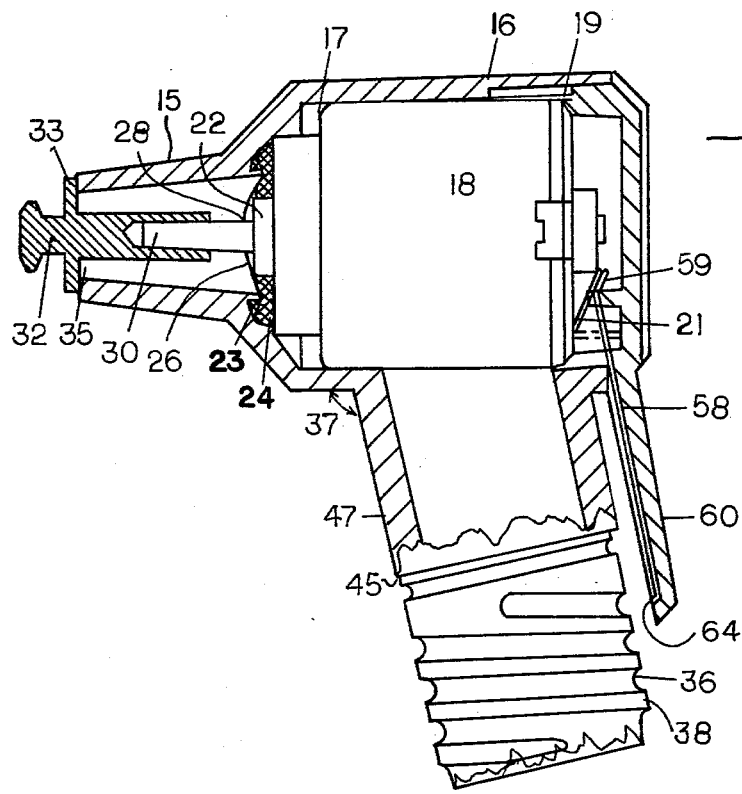
FIG. 3 is an enlarged view of the head of the dental apparatus partially shown in cross-section.
Figure 4:
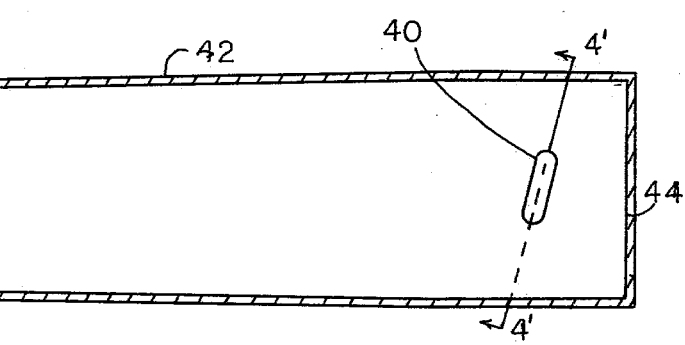
FIG. 4 is an enlarged cross-section view of the handle of the dental apparatus.
Figure 5:
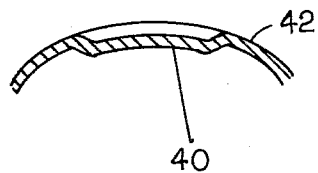
FIG. 5 is a partial enlarged cut away view of the handle attaching mechanism in FIG. 4, taken along lines 4'—4'.
Figure 6:
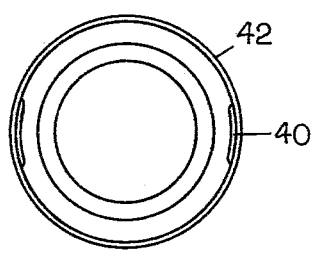
FIG. 6 is an end elevational view of the handle of FIG. 4.
Figure 7:
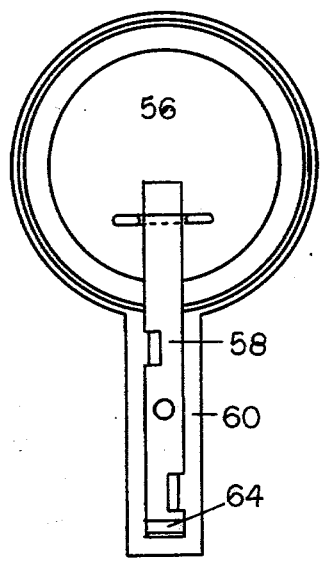
FIG. 7 is an elevational view of the switch cap of the head of the dental stain remover apparatus shown in FIG. 3.
Figure 8:
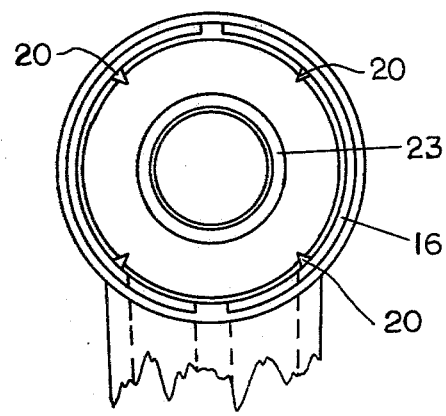
FIG. 8 is an interior elevational view of the rear of the head of the dental stain remover apparatus seen in FIG. 3.
Figure 9:
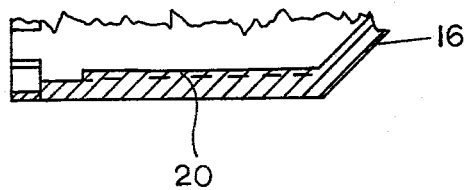
FIG. 9 is an enlarged cut away cross-sectional partial view of a portion of the head of the dental stain remover apparatus.

The base 36 of the drive casing preferably extends from the axis of the drive casing 16 at an angle of approximately 101° or 11° from a perpendicular drawn from the axis to form an obtuse angle 37 of about 100°. The base 36 can alternately be formed at an angle with the casing 16 ranging between 95° to 105° for optimum usage. The base 36 is formed with screw threads 38 which are adapted to engage inwardly projecting dimples 40 formed in a handle housing 42. The dimples 40 form a pathway to accommodate a right hand thread so that each successive thread passes over and below the dimples as the base 36 is threaded down into the handle housing. When the handle is completely threaded the end 44 of the handle abuts the base 36 at stop 45 so that the handle casing is flush with the drive base casing 47 as shown in FIG. 2. The dimples are stamped inward 0.037 inches and form a 10° angle from a perpendicular drawn from the axis of the handle. The handle housing 42 is preferably constructed of an electrically conductive metal such as brass with a chrome plated polished finish. The housing is tubularly shaped and tapered from an open smooth edge end 44 to a closed end 46 which is angled 45° at its corners to form a spring seat. A spring 52 is positioned in the spring seat and is contructed of a galvanized 16 gauge coiled spring and having a height approximately 15/37 of an inch. The batteries 48 and 50 are mounted in the handle housing and are biased in the end of the handle housing by the spring 52 which forces the batteries to electrically engage the motor surface at 54. A cap switch assembly 56 including a flexible switch lever 60 is sonically welded to the drive casing, and projects downwardly from the drive casing in substantially the same direction as the base 36. The switch lever 60 has a thin nickle coated electrically conductive metallic contact strip 58 secured thereto. One end 59 of the contact strip electrically contacts the negative pole 21 of motor 18. When the flexible switch lever 60 is pressed inward to engage the handle, the contact strip 58 secured to the lever engages the handle at contact 64 to complete a circuit throughout the instrument activating the motor turning the shaft and its respective spindle and dentifrice cup so that dentifrice can be applied to the teeth of the individual in a rotary motion.

It is important to note that the drive casing is placed at an angle with respect to the handle casing to aid in the ease of manipulation by the operator of the dental device. This angle 37 is made by the intersection of a line taken along the axis of the drive casing 30 and a line drawn through the axis of the handle. It has been found that optimum results for a wide variety of operators has been found when the angle 37 ranges from 95° to 105°. In the preferred embodiment the angle is about 100°.

The housing of the drive casing is preferrably molded in a one-piece fashion of plastic with the end cap including the switch lever being constructed of the same material and sonically welded to the head casing to form a one-piece unit at a relatively low cost. This housing is generally formed of a plastic which is chemically inert to human saliva and human contaminates found around the mouth, and is non-toxic and with high impact characteristics. One such plastic which has ben successfully used is acrylonitrile—butadrine—styrene (ABS) although other plastics of the same family of plastics can be used. The handle is constructed of a chromed brass or steel or any other suitable electrically conductive material which when connected with the conductor strip will allow a circuit to be complete activating the motor.

The cup member 34 is preferredly force fit over the male end of the spindle 32 as shown in FIG. 2 and is constructed of a rubber material which can be easily pulled off the end of the spindle and disposed of when wearing occurs due to use of the instrument.

In operation of the device the cap assembly and more particularly lever 60 is pressed against the handle so that point 64 of strip 58 makes contact with the handle completing an electrical circuit to drive the motor 18. Activation of the device provides for rotative displacement of the rubber cup 34 which is then placed in contact with the teeth of the user to remove the previously described stains through abrasive action after cup 34 has been coated and filled with the standard polishing paste which is well known in the art. The need for easy manipulation of the device necessitates that the outer diameter of the handle be a reduced dimension such as that shown in FIG. 1, namely from a ⅞" outer diameter at the closed end to a ¾" outer diameter at the open end to form a straight taper. This taper and dimension allows the apparatus to be easily manipulated and operated in one hand. When the teeth have been polished the instrument is then rinsed off and placed in any desired receptacle for subsequent use.

While the preferred embodiment of the invention has been disclosed, it is understood that the invention is not limited to such an embodiment since it may be otherwise embodied in the scope of the appended claims.

What is claimed is

1. A dental instrument for removing stains from teeth comprising a housing comprising a drive casing forming a motor chamber and an electrically conductive handle casing removably mounted to said drive casing, said handle casing and said drive casing being assembled so that an angle formed by lines drawn through the axis of the drive casing and handle casing form an angle ranging from 95°–105°, motor means including a shaft mounted within said motor chamber and adapted to be seated therein, means to hold said motor means in a substantially fixed position within said motor chamber and seal said motor means from external elements, said motor holding and sealing means comprising a neoprene washer mounted on an annular stop formed by the drive casing in the interior of said motor chamber and a teflon seal mounted around said motor shaft adjacent said neoprene washer and extending beyond said annular stop to seal said motor casing from external contaminates, electrical power means comprises batteries mounted in said handle casing engaging said motor, a cap assembly secured to said drive casing, said cap assembly compromising a cap body and a lever extending from said cap body in the same direction as said handle casing extends from said drive casing, said lever containing an electrically conductive strip extending substantially along its length, said conductive strip being electrically connected at one end to said motor means, said lever being flexible and when activated by pressure being adapted to bend causing the other end of said conductive strip to engage said electrically conductive handle casing to complete a circuit activating said motor to rotate said shaft and dental stain remover means connected to said shaft.

2. A dental instrument according to claim 1 wherein said dental stain removal means is linearly aligned with said motor shaft, said dental stain remover means comprising a rigid spindle mounted on said motor shaft and a flexible cup mounted to said rigid spindle so that activation of said motor turns said motor shaft, rigid spindle and flexible cup allowing an operator to manipulate the apparatus in one hand at varying angles to contact the teeth of the user.

3. A dental instrument in accordance with claim 2 wherein said cup is releasably mounted to said spindle, said cup means defining a conical shaped end for receiving dentifrice and a flexible other end adapted to expand around a male end defined by said spindle and resume its former memory position holding said cup to said spindle end.

4. A dental instrument according to claim 1 wherein said handle casing extends from the axis of said drive casing at an angle of about 100°.

5. A dental instrument according to claim 1 wherein said handle casing is constructed of an electrically conductive metal and said drive casing is formed of a plastic material which is chemically inert with respect to human saliva.

6. A dental instrument according to claim 5 wherein said handle casing is brass with a chrome coating and said drive casing is ABS plastic.

7. A dental instrument for removing stains from teeth comprising a drive casing forming a motor chamber and an electrically conductive handle casing removably mounted to said drive casing, said drive casing comprising a motor section, a base section, a nose section defining a through going bore therein, and a cap switch assembly, said base section angularly extending from said motor section and having a tubular configuration threaded on one end, said handle casing and said drive casing being assembled so that an angle formed by lines drawn through the axis of the drive casing and handle casing form an angle ranging from about 95° to 105°, a motor including a shaft mounted within said motor chamber on a plurality of inwardly projecting ribs defined by said drive casing, seal means holding said motor in a substantially fixed position within said motor chamber and sealing said motor from external contamination, said seal means comprising a flexible washer and a thin seal member adjacent said flexible washer surrounding said shaft, electrical power means comprising a plurality of batteries electrically connected to said motor and mounted in said handle casing, said plurality of batteries being biased by spring means mounted in said handle casing so that one of said batteries contacts said motor, said cap switch assembly comprising a cap body and a flexible lever member extending from said cap body in substantially the same direction as said handle casing extends from said drive casing, said flexible lever member being provided with an outer planar surface and having mounted to its inner surface an electrically conductive strip extending substantially along its length, one end of said strip being electrically connected to a negative pole of said motor, said flexible lever member when engaged by pressure being adapted to move toward the electrically conductive handle casing so that the other end of the conductive strip engages the electrically conductive handle casing completing a circuit activating said motor, and dental stain removal means connected to said motor shaft, said dental stain removal means comprising a spindle mounted to said shaft, said spindle defining an annular radially extending flange having a diameter greater than the aperture of the drive casing nose section bore and a male end adapted to hold a flexible rubber dentifrice holding cup member.

8. A dental instrument in accordance with claim 7 wherein said handle casing defines a plurality of inwardly projecting dimples adapted to receive and hold said threaded base section.

9. A dental instrument in accordance with claim 7 wherein said spindle male end is in the form of a ball and said cup member defines a socket adapted to receive said ball.

* * * * *